United States Patent
Barker et al.

(10) Patent No.: US 9,572,951 B2
(45) Date of Patent: Feb. 21, 2017

(54) APPARATUS FOR SUPPLYING GASES TO A PATIENT

(75) Inventors: Dean Antony Barker, Auckland (NZ); Kevin Peter O'Donnell, Auckland (NZ); Martin Paul Friedrich Kramer, Auckland (NZ); Stanislave Tatkov, Auckland (NZ); Therese Clark, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 722 days.

(21) Appl. No.: 13/643,763

(22) PCT Filed: Apr. 27, 2011

(86) PCT No.: PCT/NZ2011/000059
§ 371 (c)(1),
(2), (4) Date: Feb. 8, 2013

(87) PCT Pub. No.: WO2011/136665
PCT Pub. Date: Nov. 3, 2011

(65) Prior Publication Data
US 2013/0133651 A1    May 30, 2013

Related U.S. Application Data

(60) Provisional application No. 61/328,521, filed on Apr. 27, 2010.

(51) Int. Cl.
*A61M 16/16* (2006.01)
*A61M 16/12* (2006.01)
(Continued)

(52) U.S. Cl.
CPC ........ *A61M 16/162* (2013.01); *A61M 16/109* (2014.02); *A61M 16/1095* (2014.02);
(Continued)

(58) Field of Classification Search
CPC .............. A61M 16/00; A61M 16/0003; A61M 16/0066; A61M 16/10; A61M 16/1005;
(Continued)

(56) References Cited

U.S. PATENT DOCUMENTS

| 6,895,803 B2 | 5/2005 | Seakins et al. |
| 7,111,624 B2 | 9/2006 | Thurdor et al. |

(Continued)

FOREIGN PATENT DOCUMENTS

| DE | 10318383 B3 | 7/2004 |
| JP | S63-161973 | 7/1988 |
| JP | H11-57009 | 3/1999 |
| JP | 2006-501881 | 1/2006 |
| JP | 2008-508958 | 3/2008 |
| WO | WO 01/13981 | 3/2001 |
| WO | WO 2004/112873 | 12/2004 |
| WO | WO 2008/091164 A1 | 7/2008 |
| WO | WO 2009/145646 | 12/2009 |
| WO | WO 2009145646 A1 * | 12/2009 |

OTHER PUBLICATIONS

International Search Report; PCT/NZ2011/000059; dated Jul. 21, 2011; 4 pages.

(Continued)

*Primary Examiner* — Lynne Anderson
*Assistant Examiner* — Elliot S Ruddie
(74) *Attorney, Agent, or Firm* — Knobbe, Martens, Olson & Bear LLP

(57) ABSTRACT

An apparatus for the supply of humidified gases to a patient is disclosed that comprises a gases supply passage downstream of a humidified gases supply, and upstream of a patient in use, where at least one sensor is embedded in or located on the outside of the wall of the passage. In preferred forms the wall of the passage divides the sensor(s) from a flow of gases in the passage. In use, a controller receives an output of the sensor(s) and derives from the output of the sensor(s) an estimation of a property of gases flowing through the passage or provides a control output to the humidified gases supply according to the output of the sensor(s).

34 Claims, 10 Drawing Sheets

(51) Int. Cl.
    *A61M 16/00* (2006.01)
    *A61M 16/10* (2006.01)
(52) U.S. Cl.
    CPC .......... *A61M 16/12* (2013.01); *A61M 16/127* (2014.02); *A61M 16/16* (2013.01); *A61M 16/161* (2014.02); *A61M 2016/0021* (2013.01); *A61M 2016/0039* (2013.01); *A61M 2016/1025* (2013.01); *A61M 2202/0208* (2013.01); *A61M 2205/3368* (2013.01); *A61M 2205/3386* (2013.01)
(58) Field of Classification Search
    CPC ............ A61M 16/108; A61M 16/1045; A61M 16/1075; A61M 16/1085; A61M 16/109; A61M 16/1095; A61M 16/16; A61M 16/161; A61M 16/162; A61M 16/127; A61M 16/12; A61M 2016/0021; A61M 2016/0039; A61M 2016/1025; A61M 2202/0208; A61M 2205/3368; A61M 2205/3386
    USPC ............ 128/203.14, 203.16, 203.17, 204.17; 73/29.01
    See application file for complete search history.

(56) References Cited

U.S. PATENT DOCUMENTS

| | | | |
|---|---|---|---|
| 2002/0082486 A1* | 6/2002 | Lavery | A61B 5/01 600/300 |
| 2004/0210151 A1 | 10/2004 | Tsukashima et al. | |
| 2008/0110459 A1 | 5/2008 | Farbarik | |
| 2008/0302362 A1* | 12/2008 | Kwok | 128/203.16 |
| 2009/0223514 A1* | 9/2009 | Smith | A61M 16/1075 128/203.14 |
| 2009/0250055 A1 | 10/2009 | Radomski et al. | |

OTHER PUBLICATIONS

Japanese English Translation Examination Report; dated Dec. 24, 2014; 3 pages.
Office Action for Japanese Patent Application No. 2013-506974 mailed Aug. 26, 2015 (with brief review in English).
Australian Examination Report; dated Jul. 22, 2013; 4 pages.

* cited by examiner

APPARATUS FOR SUPPLYING GASES TO A PATIENT

CROSS-REFERENCE TO RELATED APPLICATIONS

This application is a national phase of International Application No. PCT/NZ2011/000059, filed Apr. 27, 2011, which claims priority from U.S. Provisional Application No. 61/328,521, filed Apr. 27, 2010.

BACKGROUND OF THE INVENTION

Field of the Invention

This invention relates to an apparatus for supplying a stream of heated, humidified gases to a user for therapeutic purposes. This invention particularly relates to sensors used in the apparatus for controlling the humidity of a gases stream in devices that provide humidified air for: respiratory humidification therapy, high-flow oxygen therapy, CPAP therapy, Bi-PAP therapy, OPAP therapy, etc, or humidification of gases used for insufflation or keyhole surgery.

Description of the Related Art

Devices or systems for providing a humidified gases flow to a patient for therapeutic purposes are well known in the art. Systems for providing therapy of this type (for example respiratory humidification) have a structure where gases are delivered to a humidifier chamber from a gases source. As the gases pass over the hot water, or through the heated, humidified air in the humidifier chamber, they become saturated with water vapour. The heated humidified gases are then delivered to a user or patient downstream from the humidifier chamber, via a gases conduit and a user interface.

The gases delivery system can be a modular system that has been assembled from separate units, with the gases source being an assisted breathing unit or blower unit. That is, the humidifier chamber/heater and the blower unit are separate (modular) items. The modules are in use connected in series via connection conduits to allow gases to pass from the blower unit to the humidifier unit.

Alternatively, the breathing assistance apparatus can be an integrated system, where the blower unit and the humidifier unit are contained within the same housing in use.

In both modular and integrated systems, the gases provided by the blower unit are generally sourced from the surrounding atmosphere.

A third general form of breathing assistance system, which is typically used in hospitals, is one where the breathing assistance system receives at least a portion of the gases which it uses from a central gases source, typically external to the area of use (e.g. a hospital room). A gases conduit or similar is connected between an inlet which is mounted e.g. in the wall of a patients room (or similar). The gases conduit is either connected directly to the humidifier chamber in use, or a step-down control unit or similar can be connected in series between the gases inlet and the humidifier chamber if required. This type of breathing assistance system is generally used where a patient or user may require oxygen therapy, with the oxygen supplied from the central gases source. It is common for the pure oxygen from the gases source to be blended with atmospheric air before delivery to the patient or user, for example by using a venturi located in the step-down control unit. In systems of the type where at least some of the gases are delivered from a central source, there is no need for a separate flow generator or blower—the gases are delivered from the inlet under pressure, with the step down control unit altering the pressure and flow to the required level.

An example of a known, prior art, type of modular system using atmospheric gases only is shown in FIG. 1.

In typical integrated and modular systems, the atmospheric gases are sucked in or otherwise enter a main 'blower' or assisted breathing unit, which provides a gases flow at its outlet. The blower unit and the humidifier unit are mated with or otherwise rigidly connected to the blower unit. For example, the humidifier unit is mated to the blower unit by a slide-on or push connection, which ensures that the humidifier unit is rigidly connected to and held firmly in place on the main blower unit. An example of a system of this type is the Fisher and Paykel Healthcare 'slide-on' water chamber system shown and described in U.S. Pat. No. 7,111,624. A variation of this design is a slide-on or clip-on design where the chamber is enclosed inside a portion of the integrated unit in use. An example of this type of design is described in WO 2004/112873.

One of the problems that has been encountered with systems that provide a flow of heated, humidified gases to a patient via a gases conduit and an interface is that of adequately controlling the characteristics of the gas. Clearly, it is desirable to deliver the gas to the patient (i.e. as it exits the user interface) with the gas at precisely the right temperature, humidity, flow, and oxygen fraction (if the patient is undergoing oxygen therapy) to provide the required therapy. A therapy regime can become ineffective if the gases are not delivered to the patient with the correct or required characteristics. Often, the most desirable situation is to deliver gases that are fully saturated with water vapour (i.e. at substantially 100% relative humidity) to a user, at a constant flow rate. Other types or variations of therapy regime may call for less than 100% relative humidity. Breathing circuits are not steady-state systems, and it is difficult to ensure the gases are delivered to a user with substantially the correct characteristics. It can be difficult to achieve this result over a range of ambient temperatures, ambient humidity levels, and a range of gas flows at the point of delivery. The temperature, flow rate and humidity of a gases stream are all interdependent characteristics. When one characteristic changes, the others will also change. A number of external variables can affect the gases within a breathing circuit and make it difficult to deliver the gases to the user at substantially the right temperature, flow rate and humidity. As one example, the delivery conduit between the patient or user and the humidifier outlet is exposed to ambient atmospheric conditions, and cooling of the heated, humidified gases within the conduit can occur as the gas travels along the conduit between the exit port of the humidifier chamber and the user interface. This cooling can lead to 'rain-out' within the conduit (that is, condensate forming on the inner surface of the conduit). Rain-out is extremely undesirable for reasons that are explained in detail in WO 01/13981.

In order to assist in achieving delivery of the gases stream with the gases having the desired characteristics, prior art systems have used sensors (e.g. temperature and humidity sensors) located at various positions throughout the breathing circuit. Thermistors are generally used as temperature sensors, as these are reliable and inexpensive. Humidity sensors such as the one described in U.S. Pat. No. 6,895,803 are suitable for use with systems that deliver heated humidified gases to a user for therapeutic purposes.

Patent publication WO2001/13981 describes a system for using the output of these sensors to control aspects of the humidified gases supply system. Patent publication WO 2009/145646 another system for using the output of sensors to control aspects of the humidified gases supply system. The content of this publication is hereby incorporated by reference in its entirety.

The conventional approach to providing sensors in the gases stream is to provide a probe that penetrates the tube wall. The probe extends into the gases stream. A thermistor is provided at the probe tip, usually positioned at approximately the middle of the gases stream.

The probe can be fixed in place (for example, where it is provided in a permanent location within the body of the gases supply) or as a removable probe (for example, where it is positioned in part of a replaceable component such as a breathing circuit). In the case of a removable probe, the component to which the probe attaches may include a suitable port with the probe being pushed into the port to protrude into the inside of the conduit.

Positioning the sensor portion of the probe centrally in the gases stream is thought desirable to provide a representative reading of the property of the gases stream (whether this be temperature, humidity or flow). Unfortunately, in this location, the sensor is vulnerable to efforts to clean the inside of the gases passages, for example, with a small sponge on the end of a narrow handle. Furthermore, the projecting sensor can impede the ability to fully clean the gases passage. This can be particularly the case where the protruding probe extends into the passage between an open end of the passage and a bend in the passage. The area between the bend and the probe becomes difficult to access, particularly the surface areas directly behind the probe. Attempts to access these areas can lead to damage to the probe.

SUMMARY OF THE INVENTION

It is an object of the present invention to provide a sensor arrangement, or apparatus including a sensor arrangement, which at least goes some way towards overcoming the above disadvantages.

In one aspect, the present invention consists in an apparatus for the supply of humidified gases to a patient, the apparatus comprising a humidified gases supply, a gases supply passage downstream of the humidified gases supply, and upstream of a patient in use, a sensor embedded in or located on the outside of the wall of the passage, a controller receiving an output of the sensor and adapted to derive from the output of the sensor an estimation of a property of gases flowing through the passage or to provide a control output to the humidified gases supply according to the output of the sensor; wherein the wall of the passage divides the sensor from a flow of gases in the passage.

According to a further aspect, the sensor is disposed in a recess in the exterior surface of the wall of the tube.

According to a further aspect, the recess projects into the flow path of gases flowing through the tube, to an extent not more than 30% of the diameter of the tube.

According to a further aspect, the gases passage has a diameter between 10 mm and 30 mm.

According to a further aspect, the portion of the gases passage in the immediate vicinity of the sensor is formed from a material having a thermal conductivity at 25° C. less than 1 W/mK, and most preferably less than 0.4 WmK.

According to a further aspect, the portion of the tube wall in the immediate vicinity of the sensor is made from a plastic material, such as polycarbonate or polypropylene.

According to a further aspect, the sensor is a thermistor.

According to a further aspect, a second sensor is provided at a location adjacent the first sensor, the second sensor also being located with the wall of the passage between the second sensor and gases flowing in the gases passage, the controller receiving output from the second sensor, from which the controller is adapted to determine a derivative of a physical property of gases flowing in the gases passage and to compare the derivatives derived using the first sensor and using the second sensor.

According to a further aspect, the sensor is located in a portion of the gases passage adjacent the humidified gases supply.

According to a further aspect, the humidified gases supply is contained within a housing and a portion of the gases passage passes through the housing, and the sensor is located in that portion of the gases passage within the housing.

According to a further aspect, the controller estimates the physical property of the gases flow based on the output of the sensor and based on operating conditions of the humidified gases supply.

According to a further aspect, the controller compensates for conditions of the humidified gases supply including parameters which indicate power applied in the humidified gases supply, ambient temperature inside the humidified gases supply housing, flow rate of gases supplied by the humidified gases supply through the gases passage way, power input to a flow generator in the humidified gases supply, power input to a humidifier in the humidified gases supply, power input to a controller in the humidified gases supply, or any combination thereof.

According to a further aspect, the portion of gases passage way including the sensor is formed as an elbow, with the sensor at or adjacent the turning part of the elbow.

According to a further aspect, the sensor is located in a location where liquids may accumulate in the gases passage.

According to a further aspect, an additional sensor is provided, spaced apart from the first sensor, one of the first sensor and the additional sensor being located in a location where liquids may accumulate in the gases passage and the other being located in a location where liquids will not accumulate in the gases passage, the controller being adapted to calculate an estimate of relative humidity of gases flowing through the passage on the basis of the outputs of the first and second sensor.

According to a further aspect, the sensor is located in a portion of the gases pathway that is remote from the humidified gases supply, such as at a location along a gases supply conduit to a patient, adjacent the patient or intermediate along the passage.

According to a further aspect, the humidified gases supply includes a humidifier, with a heater and a reservoir for containing a volume of water adjacent the heater.

According to a further aspect, the humidifier includes a heater plate and the reservoir comprises a removable container that contacts the heater plate in use.

According to a further aspect, the humidified gases supply includes a blower, the output of the blower being provided to an inlet of the humidifier.

According to a further aspect, the blower and the humidifier heater are arranged in the same housing.

In a further aspect, the present invention consists in an apparatus for the supply of humidified gases to a patient, the apparatus comprising a gases supply passage way defined by an inside surface of a passage wall, a sensor embedded in or contacting an outside surface of the passage wall of the passage, a controller receiving an output of the sensor and adapted to derive from the output of the sensor an estimation of a property of gases flowing through the passage, or a control output for humidified gases supply; wherein the wall of the passage separates the sensor from a flow of gases in the passage.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The term 'comprising' as used in this specification means 'consisting at least in part of', that is to say when interpreting statements in this specification which include that term, the features, prefaced by that term in each statement, all need to be present but other features can also be present.

BRIEF DESCRIPTION OF THE DRAWINGS

One preferred form of the present invention will now be described with reference to the accompanying drawings.

DETAILED DESCRIPTION OF THE PREFERRED EMBODIMENT

The present invention provides an improved sensor arrangement which is less likely to be damaged and allows for more effective cleaning of the conduit in which the sensors are located. The sensor arrangements are illustrated in FIGS. 8 to 11, and these arrangements are described in detail below. The sensors operate in conjunction with a controller which estimates the thermal characteristics of the gases flow based on the sensor outputs and prevailing conditions of the system. In some embodiments, the controller also controls aspects of operation of the system, such as the gases flow rate and power applied to a heater of a humidifier. In that case, the temperature sensor outputs can directly feed the control algorithm without any intermediate step of converting the sensor outputs to estimated temperatures. Instead, the control algorithm compensates directly for the prevailing system conditions.

General system configurations which may incorporate sensor arrangements according to the present invention are first described with reference to FIGS. 2 to 4.

Figure 1:
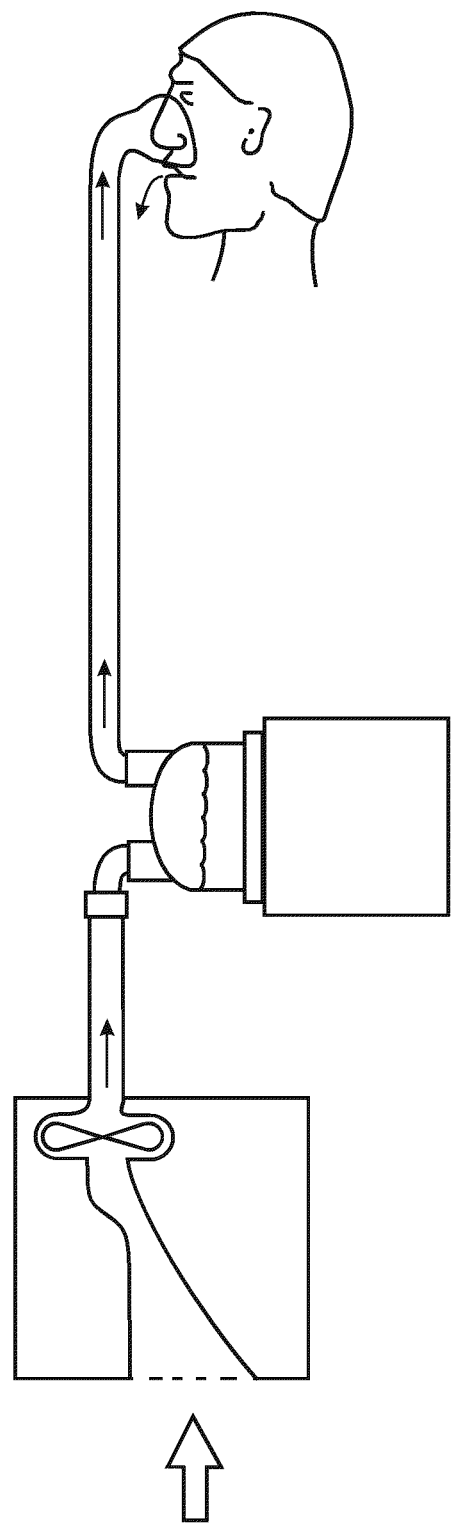
FIG. 1 shows a schematic view of a user receiving humidified air from a modular blower/humidifier breathing assistance system of a known, prior art, type.
Figure 2A:
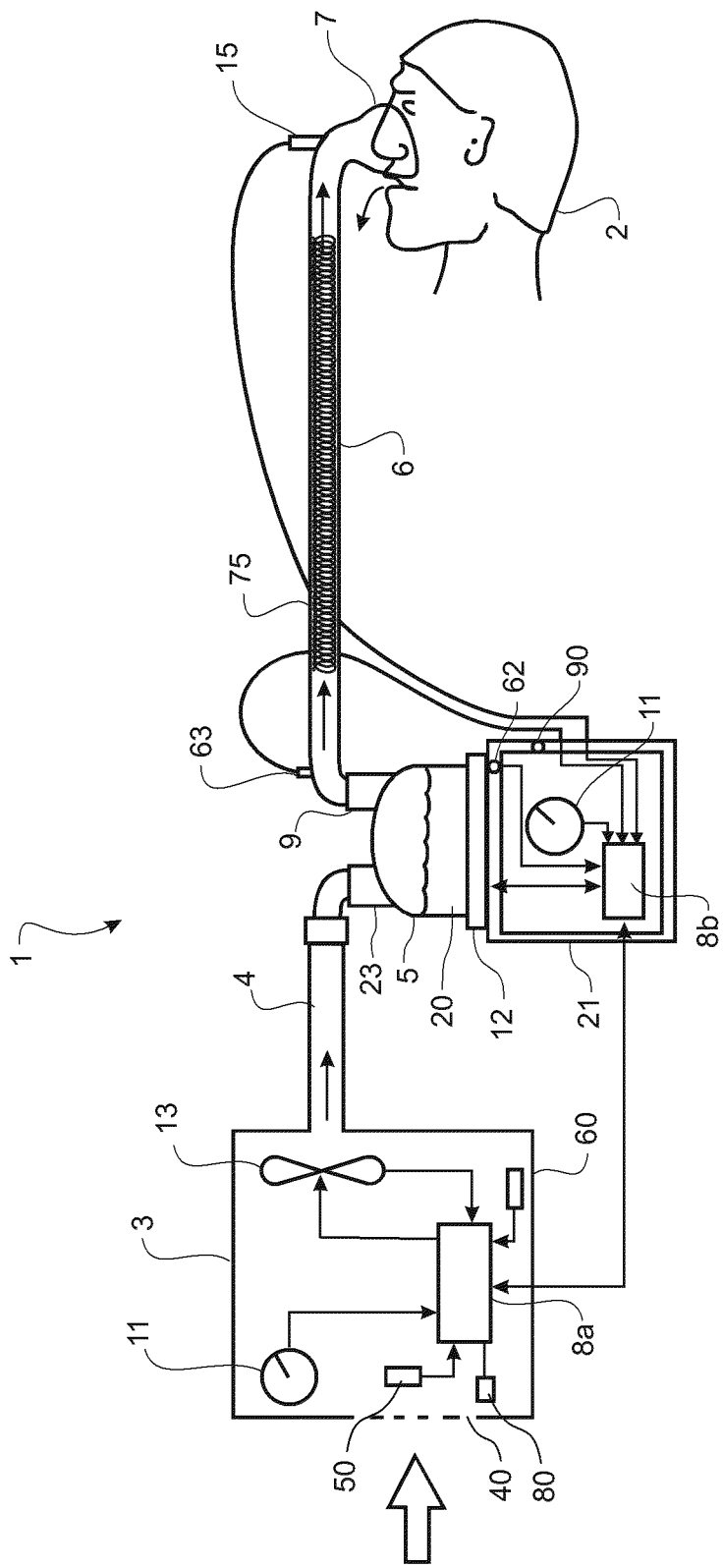
FIG. 2a shows a schematic view of a user receiving humidified air with the user wearing a nasal mask and receiving air from a modular blower/humidifier breathing assistance system.
Figure 2B:
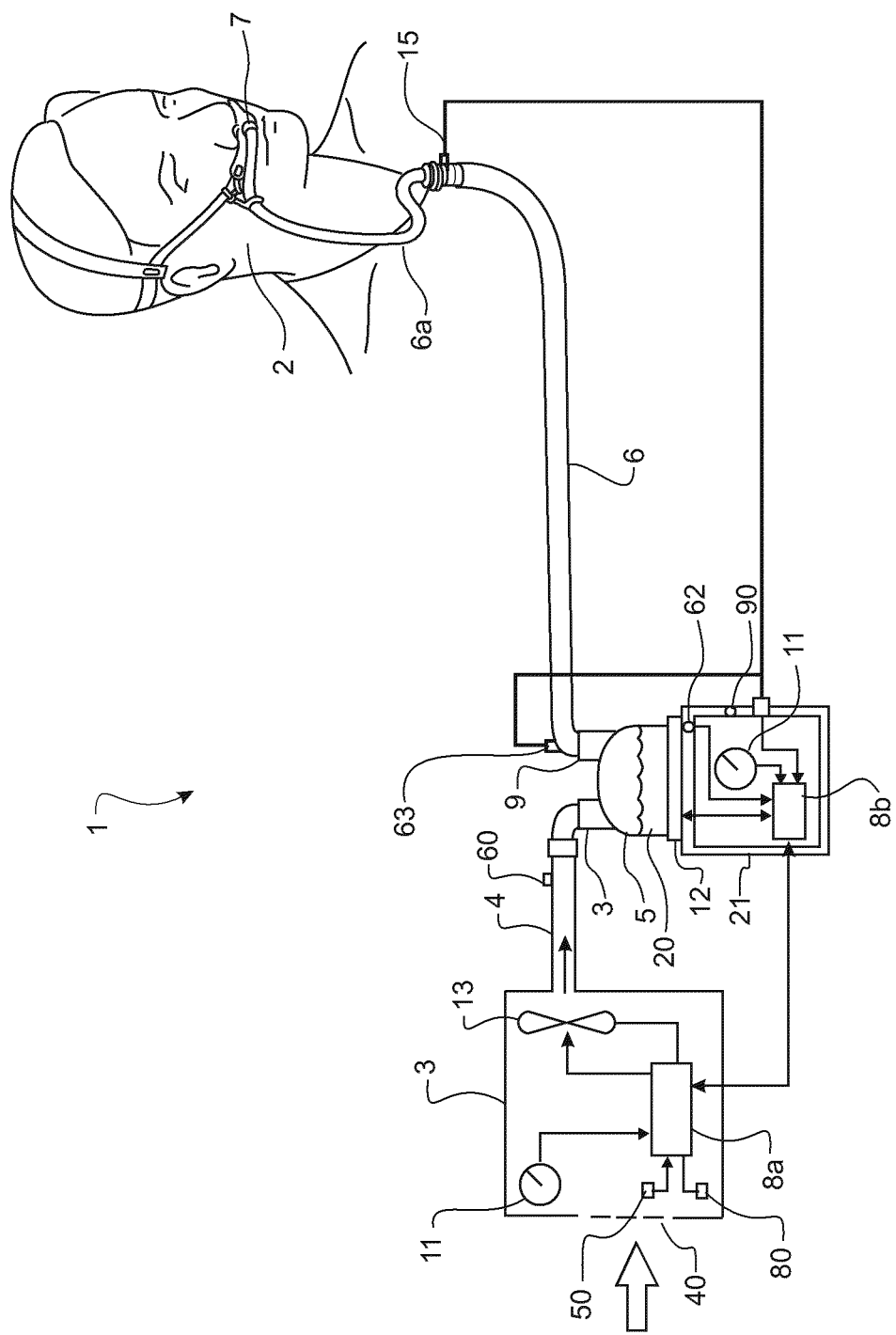
FIG. 2b shows a schematic view of a user receiving humidified air where the user is wearing a nasal cannula and receiving air from a modular blower/humidifier breathing assistance system.

A schematic view of a user 2 receiving air from a modular assisted breathing unit and humidifier system 1 according to a first example system configuration is shown in FIGS. 2a and 2b. The system 1 provides a pressurised stream of heated, humidified gases to the user 2 for therapeutic purposes (e.g. to reduce the incidence of obstructive sleep apnea, to provide CPAP therapy, to provide humidification for therapeutic purposes, or similar). The system 1 is described in detail below.

The assisted breathing unit or blower unit 3 has an internal compressor unit, flow generator or fan unit 13—generally this could be referred to as a flow control mechanism. Air from atmosphere enters the housing of the blower unit 3 via an atmospheric inlet 40, and is drawn through the fan unit 13. The output of the fan unit 13 is adjustable—the fan speed is variable. The pressurised gases stream exits the fan unit 13 and the blower unit 3 and travels via a connection conduit 4 to a humidifier chamber 5, entering the humidifier chamber 5 via an entry port or inlet port 23.

The humidifier chamber 5 in use contains a volume of water 20. In the preferred embodiment, in use the humidifier chamber 5 is located on top of a humidifier base unit 21 which has a heater plate 12. The heater plate 12 is powered to heat the base of the chamber 5 and thus heat the contents of the chamber 5. As the water in the chamber 5 is heated it evaporates, and the gases within the humidifier chamber 5 (above the surface of the water 20) become heated and humidified. The gases stream entering the humidifier chamber 5 via inlet port 23 passes over the heated water (or through these heated, humidified gases—applicable for large chamber and flow rates) and becomes heated and humidified as it does so. The gases stream then exits the humidifier chamber 5 via an exit port or outlet port 9 and enters a delivery conduit 6.

When a 'humidifier unit' is referred to in this specification with reference to the invention, this should be taken to mean at least the chamber 5, and if appropriate, the base unit 21 and heater plate 12.

The heated, humidified gases pass along the length of the delivery conduit 6 and are provided to the patient or user 2 via a user interface 7. The conduit 6 may be heated via a heater wire (not shown) or similar to help prevent rain-out. The conduit typically has a circular internal cross section. The internal diameter of the conduit is typically about 20 mm, but could be between 10 mm and 30 mm. These typical dimensions apply to both flexible portions of the gases flow passage way and rigid components such as elbows and connectors and portions integrated into components of the humidified gases supply.

The user interface 7 shown in FIG. 2a is a nasal mask which surrounds and covers the nose of the user 2. However, it should be noted that a nasal cannula (as shown in FIG. 2b), full face mask, tracheostomy fitting, or any other suitable user interface could be substituted for the nasal mask shown. A central controller or control system 8 is located in either the blower casing (controller 8a) or the humidifier base unit (controller 8b). In modular systems of this type, it is preferred that a separate blower controller 8a and humidifier controller 8b are used, and it is most preferred that the controllers 8a, 8b are connected (e.g. by cables or similar) so they can communicate with one another in use.

The control system 8 receives user input signals via user controls 11 located on either the humidifier base unit 21, or on the blower unit 3, or both. In the preferred embodiments the controller 8 also receives input from sensors located at various points throughout the system 1.

Figure 7:
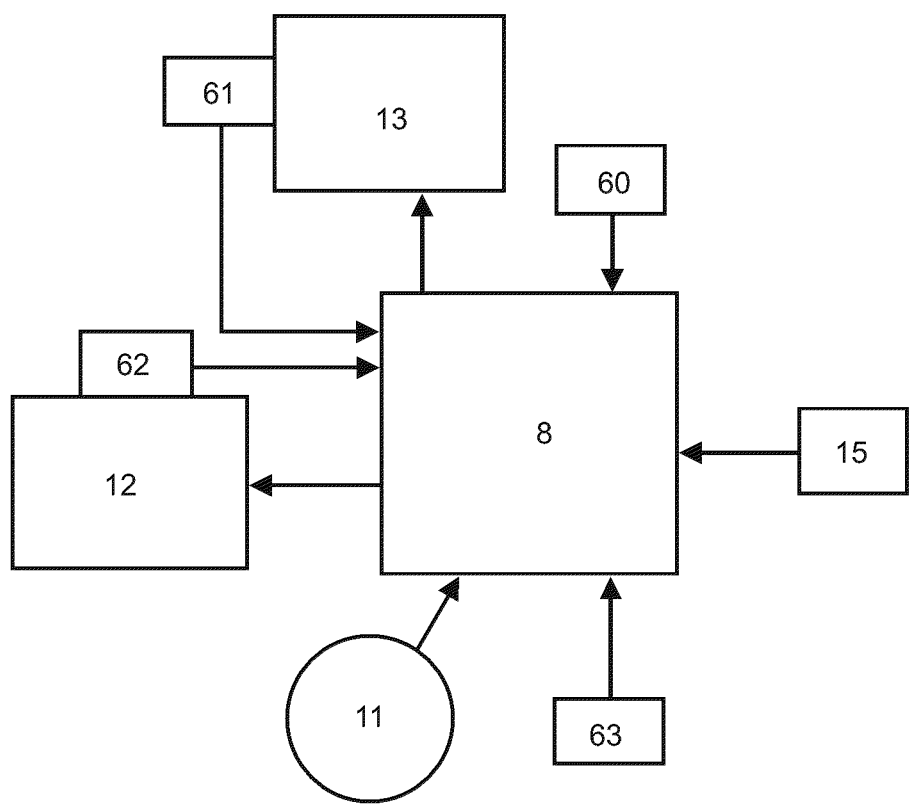
FIG. 7 shows a schematic representation of some of the connections between a controller suitable for use with the breathing assistance system of FIG. 2, 3 or 4, and other components of the preferred form of breathing assistance system as shown in FIG. 2, 3, or 4.

FIG. 7 shows a schematic representation of some of the inputs and outputs to and from the controller 8. It should be noted that not all the possible connections and inputs and outputs are shown—FIG. 7 is representative of some of the connections and is a representative example.

The sensors and their locations will be described in more detail below. In response to the user input from controls 11, and the signals received from the sensors, the control system 8 determines a control output which in the preferred embodiment sends signals to adjust the power to the humidifier chamber heater plate 12 and the speed of the fan 13. The programming which determines how the controller determines the control output will be described in more detail below.

Figure 3:
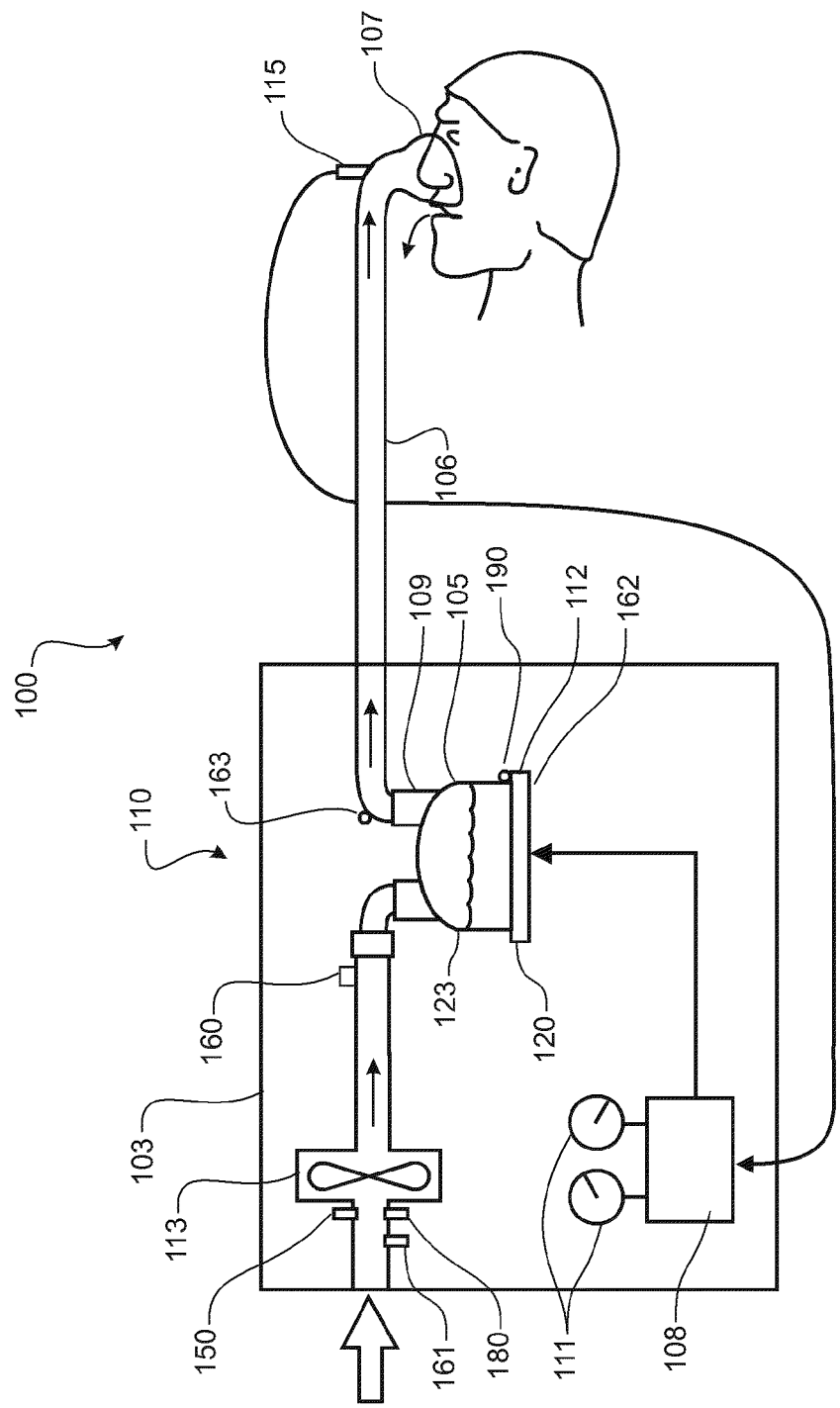
FIG. 3 shows a schematic view of a user receiving humidified air where the user is wearing a nasal mask and receiving air from an integrated blower/humidifier breathing assistance system.

A schematic view of the user 2 receiving air from an integrated blower/humidifier system 100 according to a second form of the invention is shown in FIG. 3. The system operates in a very similar manner to the modular system 1 shown in FIG. 2 and described above, except that the humidifier chamber 105 has been integrated with the blower unit 103 to form an integrated unit 110. A pressurised gases stream is provided by fan unit 113 located inside the casing of the integrated unit 110. The water 120 in the humidifier chamber 105 is heated by heater plate 112 (which is an integral part of the structure of the blower unit 103 in this embodiment). Air enters the humidifier chamber 105 via an entry port 123, and exits the humidifier chamber 105 via exit port 109. The gases stream is provided to the user 2 via a delivery conduit 106 and an interface 107. The controller 108 is contained within the outer shell of the integrated unit 100. User controls 111 are located on the outer surface of the unit 100.

Figure 4:
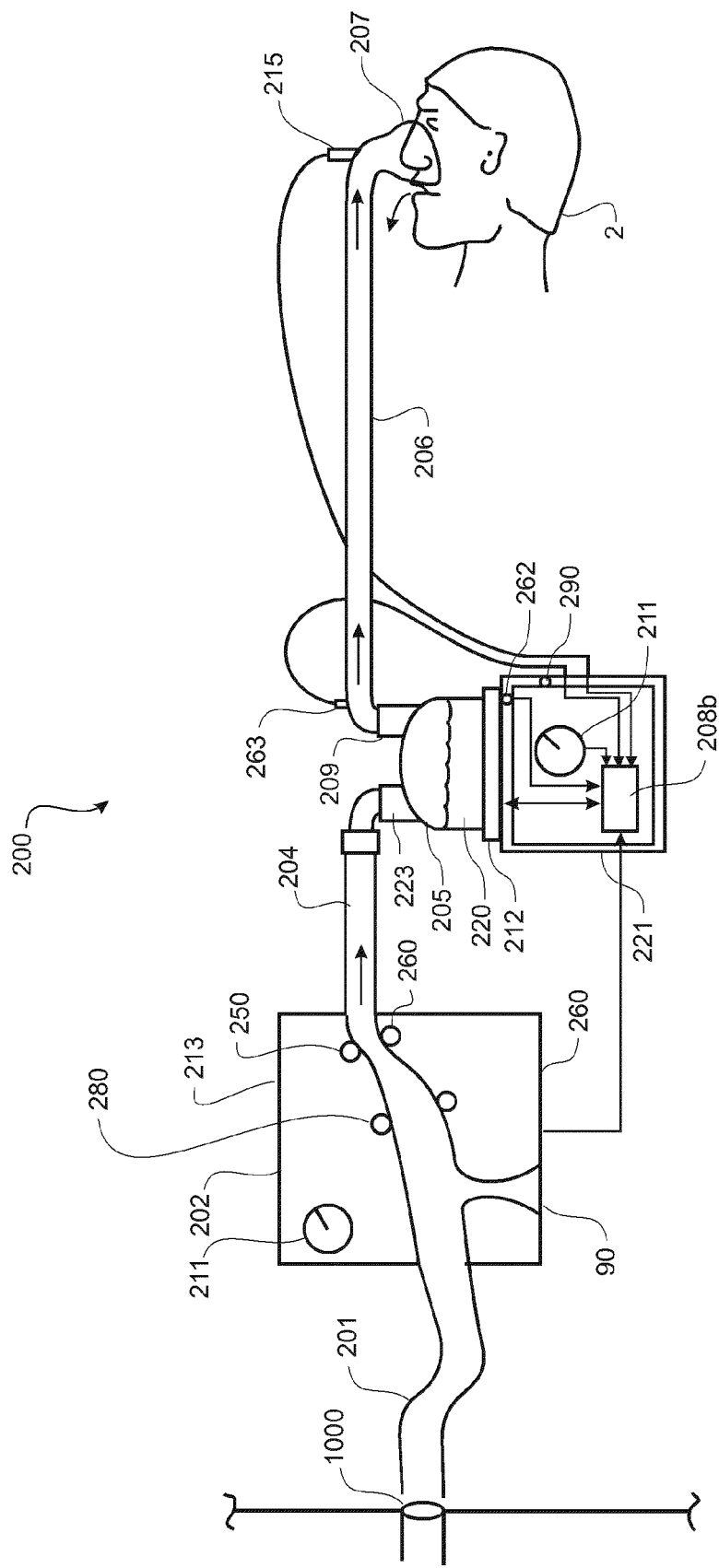
FIG. 4 shows a schematic view of a user receiving humidified air where the user is wearing a nasal cannula, the breathing assistance system receiving gases from a central source via a wall inlet and providing these to a control unit, which provides the gases to a humidifier chamber in line with and downstream of the control unit.

A schematic view of the user 2 receiving air from a further form of breathing assistance system 200 is shown in FIG. 4. The system 200 can be generally characterised as a remote source system, and receives air from a remote source via a wall inlet 1000.

The wall inlet 1000 is connected via an inlet conduit 201 to a control unit 202, which receives the gases from the inlet 1000. The control unit 202 has sensors 250, 260, 280, 290 which measure the humidity, temperature and pressure and flow respectively of the incoming gases stream.

The gases flow is then provided to a humidifier chamber 205, with the gases stream heated and humidified and provided to a user in a similar manner to that outlined above. It should be noted that when 'humidifier unit' is referred to for a remote source system such as the system 200, this should be taken to mean as incorporating the control unit 202—the gases from the remote source can either be connected directly to an inlet, or via the control unit 202 (in order to reduce pressure or similar), but the control unit and the humidifier chamber should be interpreted as belonging to an overall 'humidifier unit'.

If required, the system 200 can provide O2 or an O2 fraction to the user, by having the central source as an O2 source, or by blending atmospheric air with incoming O2 from the central source via a venturi 90 or similar located in the control unit 202. It is preferred that the control unit 202 also has a valve or a similar mechanism to act as a flow control mechanism to adjust the flow rate of gases through the system 200.

Sensors

The modular and integrated systems 1, 100 and 200 shown in FIGS. 2, 3 and 4 have sensors located at points throughout the system. These will be described below in relation to the breathing assistance system 1.

The preferred form of modular system 1 as shown in FIG. 2 has at least the following sensors in the following preferred locations:

1) An ambient temperature sensor 60 located within, near, or on the blower casing, configured or adapted to measure the temperature of the incoming air from atmosphere. It is most preferred that temperature sensor 60 is located in the gases stream after (downstream of) the fan unit 13, and as close to the inlet or entry to the humidifier chamber as possible.

2) A humidifier unit exit port temperature sensor 63 located either at the chamber exit port 9, or located at the apparatus end (opposite to the patient end) of the delivery conduit 6. Outlet temperature sensor 63 is configured or adapted to measure the temperature of the gases stream as it exits chamber 5 (in either configuration the exit port temperature sensor 63 can be considered to be proximal to the chamber exit port 9).

The sensor 63 is are preferably provided in accordance with the present invention wherein the sensor is divided from the gases flow by the wall of the tube and does not substantially protrude into the gases flow.

Similarly, sensors are arranged in substantially the same locations in the integrated system 100 shown in FIG. 3 and the system 200 of FIG. 4. For example, for the integrated system of FIG. 3, an ambient temperature sensor 160 is located within the blower casing in the gases stream, just before (upstream of) the humidifier chamber entry port 123. A chamber exit port temperature sensor 163 is located either at the chamber exit port 109 and is configured to measure the temperature of the gases stream as it exits chamber 105 (in either configuration the exit port temperature sensor 163 can be considered to be proximal to the chamber exit port 109). Alternatively, this sensor can be located at the apparatus end (opposite to the patient end) of the delivery conduit 106, for either embodiment. A similar numbering system is used for the breathing assistance system shown in FIG. 4—ambient temperature sensor 260, fan unit 213, chamber exit port temperature sensor 263 located at the chamber exit port 209, etc.

It is also preferred that the breathing assistance system 1 (and 100, 200) has a heater plate temperature sensor 62 located adjacent to the heater plate 12, configured to measure the temperature of the heater plate. The breathing assistance system(s) having a heater plate temperature sensor is preferred as it gives an immediate indication of the state of the heater plate. However, it is not absolutely necessary to for the system(s) to have the heater plate temperature sensor.

It is also most preferred that the systems have a flow probe—flow probe 61 in system 1—located upstream of the fan unit 13 and configured to measure the gases flow. The preferred location for the flow probe is upstream of the fan unit, although the flow probe can be located downstream of the fan, or anywhere else appropriate. Again, it is preferred that a flow probe forms part of the system, but it is not absolutely necessary for a flow probe to be part of the system.

The layout and operation of the breathing assistance system 1 will now be described below in detail. The operation and layout of the systems 100 and 200 is substantially the same, and will not be described in detail except where necessary.

For the breathing assistance system 1, the readings from all of the sensors are fed back to the control system 8. The control system 8 also receives input from the user controls 11.

Further alternative additional sensors and their layout will be described in more detail later.

Temperature Sensor Arrangement

According to the present invention, the temperature sensor 63 (or 163, or 263) is arranged such that the wall of the conduit divides the temperature sensor from the gases flow.

Preferably the sensor is embedded in a depression in the exterior surface of the wall of the conduit. The depression may extend so as to protrude into the gases flow. For example, the inside surface of the tube wall in the vicinity of the depression may bulge or protrude into the gases flow. Alternatively, the depression may be accommodated within the general thickness of the tube wall so that the inner surface of the tube wall in the immediate vicinity of the depression does not need to protrude relative to the surrounding inner surface. Alternatively, the sensor may be secured to the outer wall surface without an accommodating depression.

Where the depression is formed with the inner surface of the tube wall protruding into the gases flow, the degree of protrusion is preferably limited to less than ⅓ of the diameter of the conduit in that location. If the bulge that accommodates the depression protruded more than this, then the substantial benefits associated with accommodating the sensor on the outside of the conduit wall would not be achieved. Most preferably, there is no bulge or protrusion into the gases flow path associated with the sensor location. This is easier to manufacture than an arrangement with some protrusion into the flow path as the plastic mould will typically be less complex.

The perceived advantages of the sensor arrangement according to the present invention are that the conduit component is easier to mould, easier to clean and less prone to damage than with the typical prior art sensor which includes a probe protruding into the gases flow path to place the sensor component at approximately the centre of the gases flow. We have discovered that the sensor placed outside the conduit wall, or with the conduit wall between the sensor and the gases flow, can be used to adequately estimate the temperature, dew point temperature, or humidity of the gases flow where an associated controller can compensate for prevailing system conditions.

Figure 8:
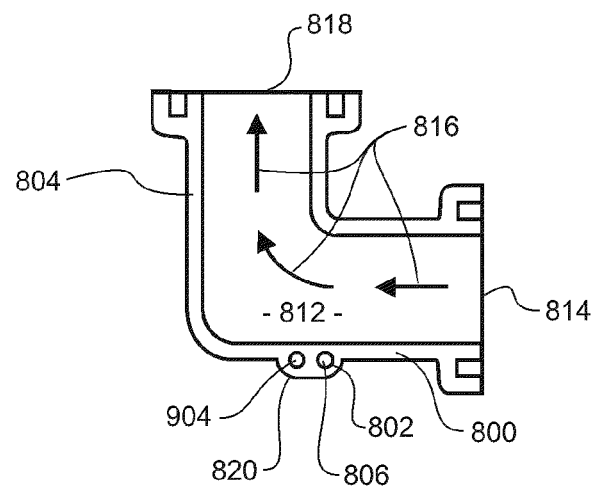
FIG. 8 is a cross-sectional side elevation of a conduit elbow incorporating a temperature sensor according to a preferred embodiment of the present invention.
Figure 9:
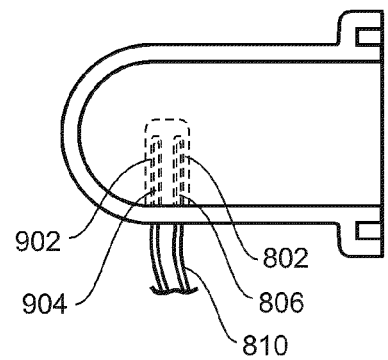
FIG. 9 is a cross-sectional top elevation of the conduit elbow of FIG. 8.

A preferred sensor implementation is illustrated in FIGS. 8 and 9. FIG. 8 illustrates a conduit elbow 800 comprising part of the gases flow path after the humidified gases leaves the humidifier. Gases enter the conduit elbow at the end 814, flow in the direction indicated by arrows 816 and exit at end 818. The elbow 800 may be constructed from any suitable plastic material. For example, the elbow may be moulded from polycarbonate. The outer surface of the connector is moulded to include a recess 802. The recess 802 is aligned across the axis of the conduit, which is best seen in FIG. 9, and is open at least one end. The recess outer surface of the elbow bulges outward (820) to accommodate the recess. The recess is separated from the gases flow by approximately one half the thickness of the wall 804 of the component. However, any separation that leaves sufficient thickness of plastic to maintain the integrity of the connector could be used.

The depression or recess may extend across or along the outside of the component to facilitate an efficient moulding tool.

A temperature sensing component 806 is located and secured in the recess 802. The temperature sensing component may be any electrical or electronic component having measurable properties that vary according to temperature. A thermistor is an example of a suitable device. The sensor may be secured in place by any suitable method. Most preferably, the sensor 806 is secured by an adhesive such as an epoxy glue or a cyanoacylate glue.

A lead 810 extends from the sensor.

In this location, the sensor is not in intimate thermal contact with the gases flow, but is in intimate thermal contact with the wall of the tube.

The internal passage 812 is not occluded by any protruding probe and the full range of the tube can be accessed for cleaning, for example, by a sponge secured to a narrow stick. There is no protruding probe which could be damaged by the attempted cleaning.

The temperature sensor is preferably located at a low point in the elbow. This location is an area that is likely to be damp due to the humidified air flow. This may improve heat transfer to the tube wall as in normal use conditions the flow is fully, or nearly fully, saturated. The control algorithms presented below have proved robust with the sensor in this location.

For many applications, safety requirements dictate a level of redundancy or the ability to check the integrity of the control system. Referring to FIG. 9, a second sensor 904 may be placed alongside the first sensor 806 and secured in place in the same way as the first sensor 806. The second sensor may reside in the same recess as the first sensor, for example, each sensor being placed at slightly spaced locations in a depression extending across the exterior of the tube. Alternatively, the conduit may be formed with slightly spaced apart recesses 802, 902 (as illustrated), with a sensor placed and secured in each recess. Leads from each sensor extend from the recess.

In this dual sensor embodiment, the controller may directly compare the sensor outputs, or may be calibrated to independently calculate a derivative of each sensor output based on system conditions, and then compare the results. If the sensor outputs, or the derivative of the sensor outputs, are significantly different, the controller will indicate an error, or will operate in a safety mode, or both. As the sensors are located in slightly different locations, comparisons of a derivative of each sensor output are preferred. Each derivative would be independently calculated according to system conditions, with the calculation being calibrated according the particular sensor location.

Figure 10:
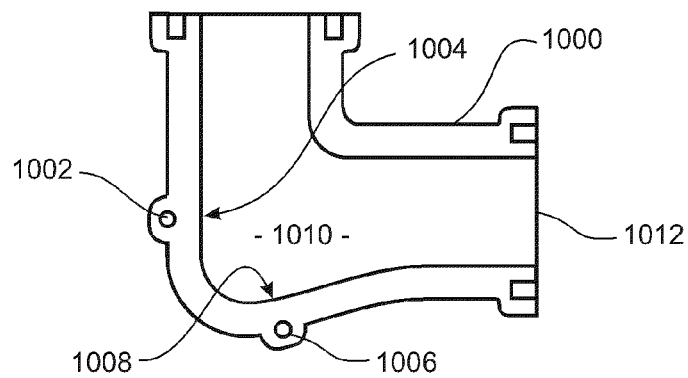
FIG. 10 is a cross-sectional side elevation of a conduit elbow incorporating a pair of sensors that may be useful to determine humidity.

A further embodiment incorporating multiple sensors is illustrated in FIG. 10. According to the arrangement of FIG. 10, the sensors are provided at spaced apart locations that are specifically intended to see different operating conditions. In particular, the arrangement of FIG. 10 provides one temperature sensor 1002 on the external surface of the conduit 1000 at a location 1004 where the conduit can be expected to be free of any accumulated condensation, and another sensor 1006 on the exterior surface of the conduit at a location 1008 where the inner surface of the conduit can be expected to accumulate condensation.

In the particular arrangement, the sensors are provided in the vicinity of a flow elbow, and the elbow is arranged such that the curve 1010 of the elbow is slightly lower 1012 than the lower of the two ends of the elbow.

The second sensor 1006 is provided in the outside of the tube wall at the location of the lowest extent of the inside surface of the tube wall. It is at that location 1008 that surface moisture is most likely to accumulate in operation of the humidified gases delivery apparatus.

The first sensor 1002 is provided at another location 1004 along the external surface of the elbow. The location of the first sensor is less constrained, but could, for example, be at a location where the inner surface of the conduit is substantially vertical in use such that condensation droplets are less likely come to rest at the location. So for example, the first sensor could reside at any of the location on the upward leg of the elbow, or at any location along the mid-point of the sides of the lower leg of the elbow.

The controller may be programmed to use the outputs from the first and second sensor in this arrangement to estimate the humidity of the gases stream. The first sensor may be used by the controller programme to estimate the temperature of the gases stream. The second sensor may be influenced by evaporation of the accumulated condensation by the gases flow and may approximate a wet-bulb sensor in a humidity sensor. Each sensor is subject to external influences of the system, including gas flow rates and ambient heating effects. The controller could compensate for these effects in the same fashion as is described below in relation to the single temperature sensor.

Where redundancy is required, multiple sensors may be provided in each location, as has been discussed above in relation to FIG. 8.

Humidity Control Method

The preferred control system 8 has at least one data set pre-loaded into the controller. The data that forms the data set is pre-measured or pre-calculated under controlled conditions (e.g. in a test area or laboratory) for a specific system configuration with specific components (e.g. system 1 or system 100, or system 200, with a particular, specific blower unit and humidifier unit used to gather the data). The data is gathered under a number of condition ranges that will typically be encountered in use, with the pre-measured (pre-set) data then being loaded as integral software or hardware into the controller 8 for the production systems, or as data to be used in e.g. a fuzzy logic algorithm for humidity control.

Figure 5:
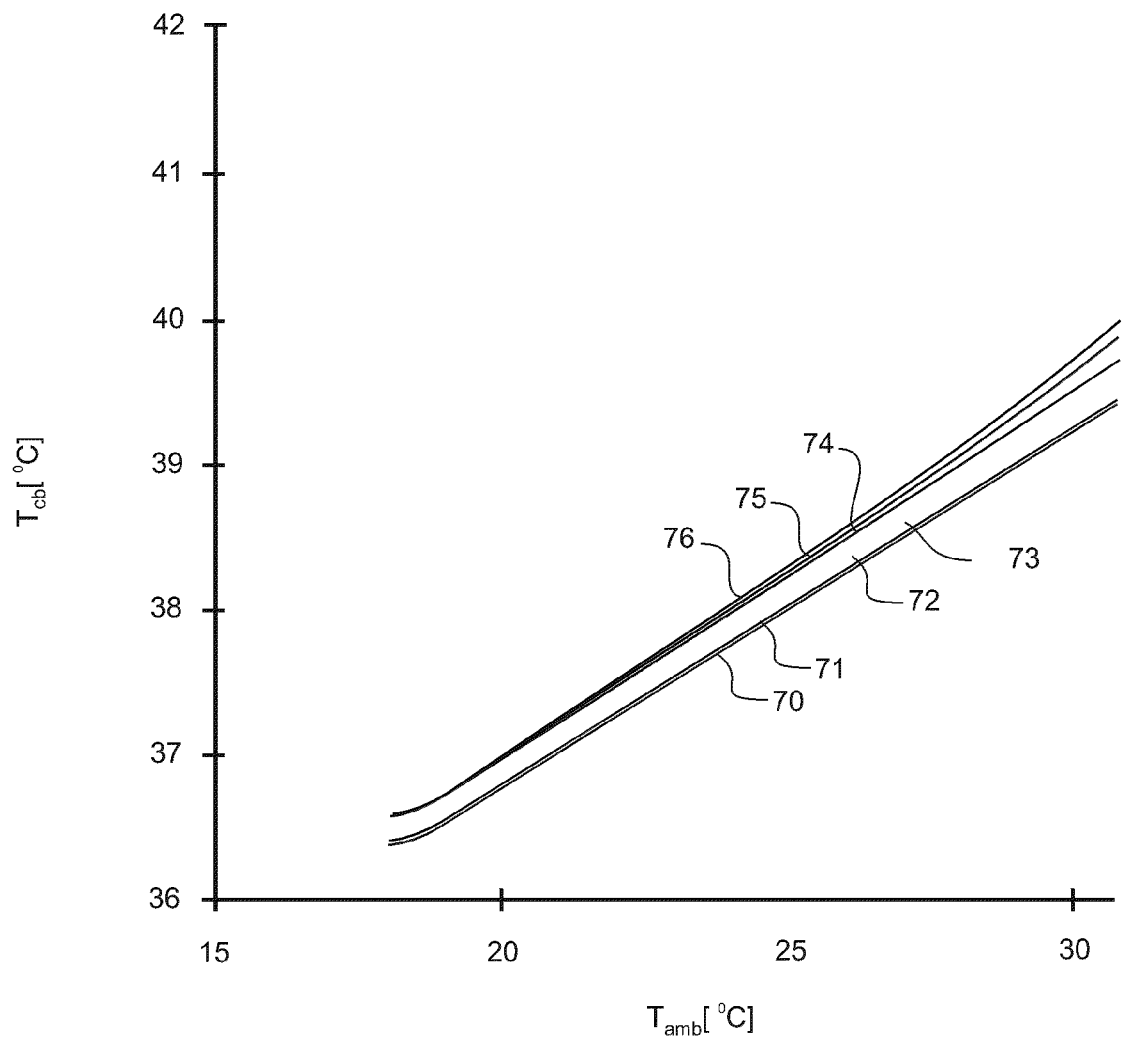
FIG. 5 shows a graphical representation of a data set for use with the breathing assistance system of FIG. 2 or 3, the graph showing curves representative of seven different constant flow rates over a range of ambient atmospheric temperatures, and a range of target temperatures for a given flow and ambient temperature, the data loaded into the system controller in use.
Figure 6:
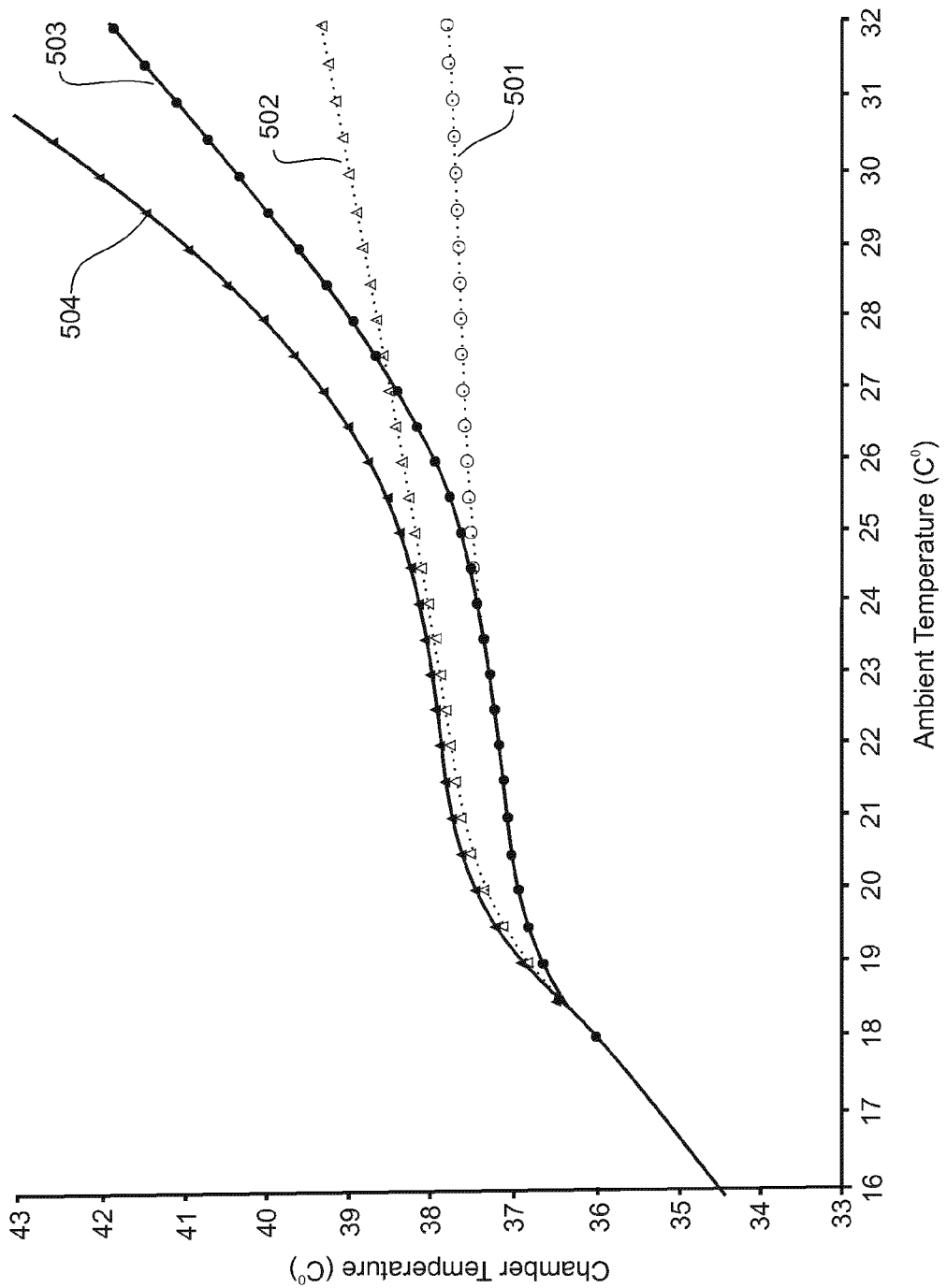
FIG. 6 shows a graphical representation of an alternate data set for use with the breathing assistance system of FIG. 2, 3 or 4, the alternative data compared to or used alongside the equivalent data from the table shown graphically in FIG. 5, the graph lines showing curves representative of two different steady flow rates for a range of ambient atmospheric temperatures with little movement of the ambient air, and a range of target temperatures for a given flow and ambient temperature, and the same steady flow rates shown over a range of ambient temperatures with high convective heat loss from the humidification chamber, the data from the look-up table loaded into the system controller in use.

A data set particularly suitable for use with system 1 is shown as a graph in FIG. 5. The X-axis shows a range of ambient temperatures, from 18° C. to 35° C. In use, the ambient temperature of the gases in the breathing assistance system before or upstream of the chamber 5 is measured by the ambient temperature sensor 60, and the ambient temperature data is relayed to the controller 8. It is most preferred that the temperature sensor 60 measures the ambient temperature of the gases just before the gases enter the chamber 5. In order to create the data set, a typical system 1 is placed in an environment where the ambient temperature can be kept at a known, constant level over a range of temperatures.

In use, a user chooses a flow rate by adjusting the controls 11. The controller 8 receives the input from the user controls 11 and adjusts the fan speed to substantially match this requested flow rate (either by altering the speed of the fan to a speed that is known to substantially correspond to the required flow for the particular breathing circuit configuration, or by measuring the flow using flow probe 61 and using a feedback mechanism via controller 8 to adjust the flow rate to the level required or requested). Seven different constant flow rates are shown in the graph of FIG. 5, for seven different constant fan speeds. The lines 70-76 correspond to different flow rates as follows: Line 70—a flow rate 15 liters/minute. Line 71—a flow rate of 20 liters/minute. Line 72—a flow rate of 25 liters/minute. Line 73—a flow rate of 30 liters/minute. Line 74—a flow rate of 35 liters/minute. Line 75—a flow rate of 40 liters/minute. Line 76—a flow rate of 45 liters/minute.

The Y-axis shows a range of target chamber temperature. These temperatures may be stored as temperature sensor values, which do not need to accord with actual calibrated temperatures. That is, for any given fan speed (flow rate and pressure), and any given ambient temperature, there is a 'best', or 'ideal' target outlet temperature for the gases in the chamber 5 above the water 20—the target outlet temperature as shown on the Y-axis. This 'ideal' temperature is the dew point temperature for a given constant flow and constant ambient temperature. That is, the temperature at which the gases can exit the chamber 5 at the required saturation (required level of humidity) and then be delivered to the user 2 at the correct temperature and pressure for effective therapy. As the gases exit the chamber 5, a temperature is measured by the chamber exit port temperature sensor 63. The controller 8 is adapted to receive the temperature data measured by the chamber exit temperature sensor 63 and the data relating to the temperature of the gases entering the chamber 5 (as measured by ambient temperature sensor 60). The flow rate has been previously set to a constant value, as outlined above, so the controller 8 already 'knows' the constant flow rate. As the controller 8 'knows' both the flow rate and the ambient temperature, it can, for example, look up an 'ideal' target outlet temperature reading from the range incorporated into the pre-loaded data set (e.g. the data shown graphically in FIG. 5). The controller 8 then compares the measured value of chamber exit temperature to the 'ideal' target chamber temperature for the given, known flow rate and ambient temperature. If the measured value of target temperature does not match the 'ideal' target value, the controller 8 generates or determines a suitable control output, and adjusts the power to the heater plate accordingly, either increasing the power to increase the temperature of the gases within the chamber 5, or decreasing the power to decrease the gases temperature. The controller 8 adjusts the power in this manner in order to match the temperature measured at the outlet or exit port with the required target temperature. In the preferred embodiment, the mechanism by which the controller 8 adjusts the output characteristics is via a Proportional-Integral-Derivative controller (P.I.D. controller) or any one of a number of similar mechanisms which are known in the art.

The controller could also generate or determine a suitable control output by, for example, using a fuzzy logic control algorithm loaded into the controller 8, or mathematical formulae which utilise the measured temperature and flow data as variables in the equations.

Examples of mathematical formulae are shown below. These correspond generally to the data shown graphically in FIG. 5, for the range of flow rates from 15 to 45 liters/min.

15LPM: $T_{cs} = -6E\text{-}06 T_{amb}^5 + 0.0008 T_{amb}^4 - 0.0421 T_{amb}^3 + 1.0953 T_{amb}^2 - 13.873 T_{amb} + 103.97$ 20LPM: $T_{cs} = -6E\text{-}06 T_{amb}^5 + 0.0008 T_{amb}^4 - 0.0421 T_{amb}^3 + 1.0947 T_{amb}^2 - 13.865 T_{amb} + 103.97$ 25LPM: $T_{cs} = -6E\text{-}06 T_{amb}^5 + 0.0008 T_{amb}^4 - 0.0421 T_{amb}^3 + 1.0951 T_{amb}^2 - 13.871 T_{amb} + 104.06$ 30LPM: $T_{cs} = -6E\text{-}06 T_{amb}^5 + 0.0008 T_{amb}^4 - 0.0422 T_{amb}^3 + 1.0971 T_{amb}^2 - 13.896 T_{amb} + 104.25$ 35LPM: $T_{cs} = -8E\text{-}06 T_{amb}^5 + 0.001 T_{amb}^4 - 0.0544 T_{amb}^3 + 1.4001 T_{amb}^2 - 17.595 T_{amb} + 122.06$ 40LPM: $T_{cs} = -1E\text{-}05 T_{amb}^5 + 0.0014 T_{amb}^4 - 0.0726 T_{amb}^3 + 1.8513 T_{amb}^2 - 23.102 T_{amb} + 148.55$ 45LPM: $T_{cs} = -1E\text{-}05 T_{amb}^5 + 0.0017 T_{amb}^4 - 0.0877 T_{amb}^3 + 2.2264 T_{amb}^2 - 27.679 T_{amb} + 170.55$ Example: the therapy regime of a user 2 specifies a certain flow rate and pressure, for example a flow of 45 liters/min. The speed of the blower or fan unit 13 is set (via the controls 11) to deliver gases at this flow rate. If a flow probe 61 is part of the system, this flow rate can be dynamically adjusted by feeding back a real-time flow reading from the flow sensor or flow probe 61 to the controller 8, with the controller 8 adjusting the fan speed as necessary. This can be done via a P.I.D. controller that comprises part of the controls 8 as described in detail below, or similar. It is preferred that the flow rate is dynamically adjusted and monitored. However, if a flow probe is not part of the system, then the flow rate is assumed or calculated from the fan speed, and is assumed to be constant for a constant fan power level. The flow rate of 45 liters/minute is shown by line 76 on the graph of FIG. 5. In this example, the user 2 is sleeping in a bedroom having an ambient temperature of substantially 30° C. Air at 30° C. enters the breathing assistance apparatus and as it passes through the fan and connecting passages within the casing, it warms up slightly. The temperature of the air just before it enters the humidifier chamber is measured by the ambient temperature sensor 60. As the ambient temperature and the flow rate are known, the controller 8 can calculate the required target temperature, as shown on the Y-axis of the graph of FIG. 5. For this particular example, it can be seen that the chamber target temperature is 39.4° C. The chamber exit temperature sensor 63 measures a temperature at the exit of chamber 5 (the gases temperature at the exit point will be substantially the same temperature as the gases in the space above the chamber contents 20). If the gases temperature as measured by the chamber exit temperature sensor 63 is not 39.4° C., then the controller 8 determines and generates a suitable control output which alters the power to the heater plate 12 accordingly. As above, if the ambient temperature as measured by the ambient temperature sensor 60 changes, this can be fed back to the controller 8 and the outputs altered as appropriate using a P.I.D. control algorithm or similar.

One of the advantages of this system over the systems disclosed in the prior art is as follows: in prior art systems, as the ambient temperatures approach the target dew point temperature, the heater plate will draw less power and not raise the temperature of the water in the humidifier chamber as much. Therefore the gases will tend not to be fully saturated as they exit the chamber. The method outlined above overcomes this problem by using values of ambient temperature or more preferably chamber inlet temperature, chamber exit temperature and flow rate for a system of a known configuration, in order to produce a target chamber exit temperature which is considered to be substantially the best or 'ideal' temperature for gases saturation and delivery to a user for a set flow rate and a particular ambient temperature.

Another advantage is that the system 1 can accurately control the humidity level without the need for an accurate humidity sensor.

Another advantage is that when gas is delivered to the humidifier chamber from the compressor or blower, and this incoming gas has an increased temperature, the chamber temperature can be accurately compensated to achieve the desired dew point. This is particularly advantageous if the air or gases entering the chamber are warm, and also in situations when the temperature increases as the flow increases. In operation, any flow generator causes an increase in air temperature between the inlet from atmosphere and the outlet. This change in temperature can be more pronounced in some types of flow generator. The temperature of components of the system can change between the time at which the system is first activated and some time afterwards (e.g. over a reasonably prolonged period of time such as 1-2 hours). That is, components of the system can heat up as the system is operating, with the system taking some time to reach a steady state of operation. If these components are located in or adjacent to the air path between the point at which air enters the system, and the point at which the air enters the chamber, then the temperature of these gases is going to change—there is going to be some heat transfer from these components to the gases as the gases travel along this path. It can therefore be seen that measuring the temperature of the gases as they enter the chamber reduces the likelihood of introducing a temperature measurement error into the control calculations, as the temperature of the gases at the point of entry to the system when the system has reaches a steady state of operation may be different from the temperature of the gases at the point of entry to the chamber. However, it has generally been found that although it is most preferable to measure gases temperature at the point of entry to the chamber, it is also acceptable in most circumstances to measure atmospheric gases temperature.

The method described above is substantially similar for the integrated apparatus 100, or the apparatus 200, although the pre-set or pre-measured and pre-loaded values in the look-up table may differ as the apparatus has a slightly different configuration. In other forms, the user could choose a pressure rate (and the data set would be modified for pressure values rather than flow values).

Further Alternative Sensor Layouts

In a variant of the apparatus and method outlined above, the system (system 1 or system 100 or system 200) also has additional sensors as outlined below.

1) A patient end temperature sensor 15 (or 115 or 215) is located at the patient end of the delivery conduit 6 (or alternatively in or on the interface 7). That is, at or close to the patient or point of delivery. When read in this specification, 'patient end' or 'user end' should be taken to mean either close to the user end of the delivery conduit (e.g. delivery conduit 6), or in or on the patient interface 7. This applies unless a specific location is otherwise stated. In either configuration, patient end temperature sensor 15 can be considered to be at or close to the user or patient 2.

Figure 11:
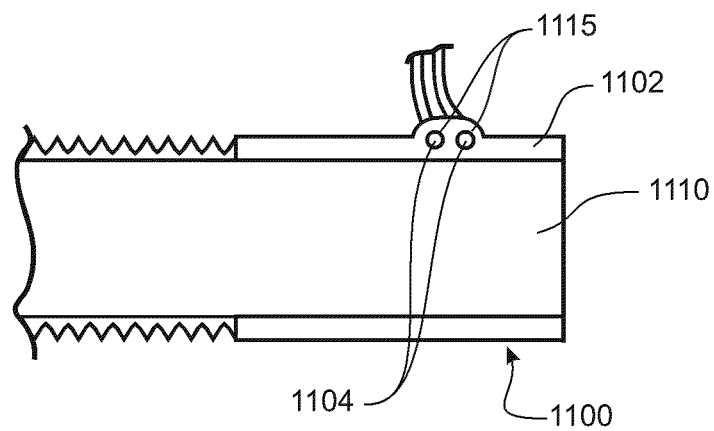
FIG. 11 is a cross-sectional side elevation of a connector cuff including a temperature sensor according to another embodiment of the present invention.

These sensors are preferably provided in accordance with the arrangement of the present invention. The sensors are divided from the gases flow by the wall of the tube and do not substantially protrude into the gases flow. As illustrated in FIG. 11, the temperature sensor 1115 may be provided such that the wall 1102 of the connector 1100 lies between the temperature sensor and the gases flow with an equivalent construction to that described in FIGS. 8 and 9. So, for example, the illustrated connector includes a pair of recesses 1104 spaced apart across the external surface. A sensor 1115, for example, a thermistor, is located in each recess. Each sensor 1115 is secured in the recess by a suitable adhesive such as epoxy glue.

According to this arrangement, the interior of the conduit is not occluded by any protruding probe. According to this arrangement, the sensor is not exposed to the gases stream, so it does not require any subsequent sterilisation or treatment. Furthermore, the inside surface of the conduit may be more easily cleaned. Alternatively, a peel-away sleeve 1110 may be provided to the inner surface of the conduit without being obstructed by a protruding sensor. The peel-away sleeve could be stripped out of the conduit after a first use so that the conduit could be re-used, either with a new peel-away sleeve having been inserted (such that the conduit can be used many times) or without a peel-away sleeve so that the conduit can be used a single extra time. Multiple layers of peel-away sleeves could be initially incorporated so that the conduit can be accordingly re-used multiple times.

Figure 12:
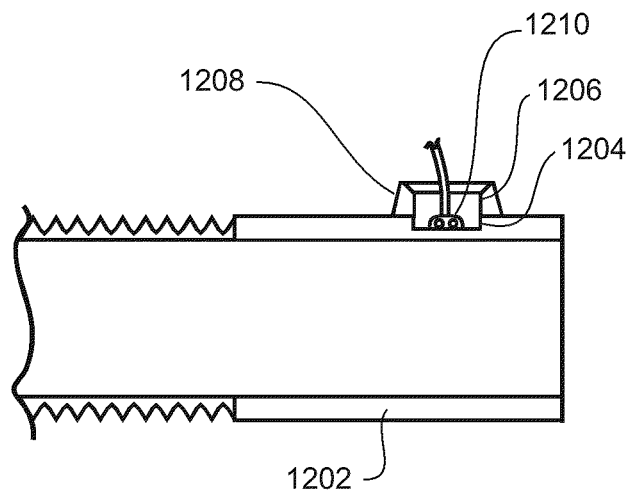
FIG. 12 is a cross-sectional side elevation of a connector cuff including a temperature sensor according to another embodiment of the present invention.

Referring to FIG. 12, the sensors provided to the outside of the tube wall may be incorporated in a housing detachable from the tube wall. For example, the conduit connector 1202 may include a depression suitable for accommodating the housing component 1206. Securing features, in the form of a taper, lip or clips (1208) may locate the housing component 1206 in the depression 1204. The sensors 1210 may be provided in the housing component in a location that would be adjacent the surface of the depression 1204 when the housing component is located in the depression. According to this arrangement, the sensors can be re-used even though the conduit is disposable.

The reading from the patient end temperature sensor 15 is fed back to the controller 8 and is used to ensure that the temperature of the gases at the point of delivery substantially matches the target patient temperature of the gases at the chamber exit (the target patient temperature is the target dew point temperature at the chamber exit). If the reading from the patient end temperature sensor 15 indicates that the gases temperature is dropping as it travels the length of the delivery conduit 6, then the controller 8 can increase the power to the conduit heater wire (shown as wire 75 on FIG. 2*a*—not shown but present in the alternative preferred forms of breathing assistance system 200 and 400 shown in FIGS. 3 and 4, and the system shown in FIG. 2*b*) to maintain the gases temperature. If the power available to the conduit heater wire 75 is not capable of allowing the gases at the point of delivery to equal the dew point temperature at the chamber exit 9 then the controller 8 lowers the target chamber exit temperature (to lower the dew point temperature). The controller 8 lowers the chamber exit temperature to a level at or close to the maximum gases temperature the conduit heater wire is able to deliver to the patient as measured by the patient end temperature sensor 15. The controller 8 is loaded with a predetermined data set, and adjusts the power to the heater plate, or the conduit heater wire, or both, by using this data (which is similar to that shown in graphical form in FIG. 5). For a constant flow level and for a measured ambient temperature as measured by ambient temperature sensor 60 (which may change), there is an ideal patient end temperature. The controller 8 adjusts the power output or outputs of the heater plate and the conduit to match the temperature at the patient end of the conduit (as measured by temperature sensor 15) with this ideal temperature.

The above method can be further refined for accuracy if other conditions of the gases in the system are known—the gases conditions. For example, if the humidity level of the incoming gases to the blower is known, or the gases pressure of the incoming gases. In order to achieve this, alternative embodiments of the systems 1, 100 and 200 described above can also have a gases condition sensor located in the incoming gas path (e.g. a humidity sensor or a pressure sensor). For the modular system 1, a humidity sensor 50 is shown located proximal to the atmospheric inlet 40. For the integrated system 100, this is shown as humidity sensor 150 (and so on). In a similar fashion to the control methods outlined above, the controller 8 is pre-loaded with a humidity level data set. For a constant flow rate, and known ambient or external humidity level, there is an ideal gases temperature at the chamber exit (or at the point of delivery to a user). The data set contains these ideal values for a range of ambient humidities and flow rates, similar to the values shown in graphical form in FIG. 5. The controller 8 adjusts the power output of the heater plate, or the heater wire, or both, to match the measured chamber exit temperature reading (or patient end temperature) with the 'ideal' temperature reading retrieved from the data set in the memory of the controller). In a similar manner, the above method can be refined for accuracy if the pressure level of the incoming gases to the humidification chamber blower is known, locating a pressure sensor in the incoming gas path to the humidification chamber (pressure sensor 80 shown in the incoming gases path in FIG. 2 for the modular system. Pressure sensor 180 is shown in the incoming gases path in FIG. 3 for the integrated system. Pressure sensor 280 is shown in the incoming gases path in FIG. 4 for the central gases source system). It should be noted that if the data for the data set was plotted graphically for conditions of constant flow, ambient temperature and another gases condition (e.g. humidity or pressure), the graphs would be required to be plotted on three axes—X, Y and Z—the graphs would be 'three-dimensional' when plotted.

The invention claimed is:

1. An apparatus for the supply of humidified gases to a patient, the apparatus comprising:
 a humidified gases supply,
 a gases supply passage downstream of the humidified gases supply and upstream of a user interface, the gases supply passage comprising a wall having an outside, and an inner surface first and second temperature sensors embedded in or located on the outside of the wall of the gases supply passage, and does not extend through the inner surface of the wall of the gas supply passage a controller receiving outputs from the sensors and adapted to derive from the outputs of the sensors an estimation of humidity of gases flowing through the gases supply passage and to provide a control output to the humidified gases supply according to the outputs of the sensors;

wherein at least the inner surface of the wall of the gases supply passage separates the sensors from a flow of gases in the gases supply passage such that the sensors sense temperature of the gases supply through at least the inner surface of the wall of the gases supply passage.

2. An apparatus as claimed in claim 1, wherein the sensors are disposed in a recess in an exterior surface of the wall of the gases supply passage.

3. An apparatus as claimed in claim 2, wherein the recess projects into a flow path of gases flowing through the gases supply passage to an extent not more than 30% of a diameter of the gases supply passage.

4. An apparatus as claimed in claim 3, wherein the diameter of the gases supply passage is between 10 mm and 30 mm.

5. An apparatus as claimed in claim 2, wherein a portion of the gases supply passage in an immediate vicinity of the sensors is formed from a material having a thermal conductivity at 25° C. less than 1 W/mK.

6. An apparatus as claimed in claim 5, wherein the portion of the wall of the gases supply passage in the immediate vicinity of the sensors is made from a plastic material.

7. An apparatus as claimed in claim 1, wherein the second sensor is provided at a location adjacent the first sensor, the controller receiving the output from the second sensor from which the controller is adapted to determine a derivative of a physical property of gases flowing in the gases supply passage and to compare the derivatives derived using the first sensor and using the second sensor.

8. An apparatus as claimed in claim 1, wherein the sensors are located in a portion of the gases supply passage adjacent the humidified gases supply.

9. An apparatus as claimed in claim 8, wherein the humidified gases supply is contained within a housing and a portion of the gases supply passage passes through the housing such that the portion of the gases supply passage is positioned within the housing, and the sensors being located in the portion of the gases supply passage positioned within the housing.

10. An apparatus as claimed in claim 9, wherein the controller estimates the humidity of the gases flowing through the gases supply passage based on the outputs of the sensors and based on operating conditions of the humidified gases supply.

11. An apparatus as claimed in claim 10, wherein the controller compensates for conditions of the humidified gases supply including parameters that indicate power applied in the humidified gases supply, ambient temperature inside the housing of the humidified gases supply, flow rate of gases supplied by the humidified gases supply through the gases supply passage, power input to a flow generator in the humidified gases supply, power input to a humidifier in the humidified gases supply, power input to a controller in the humidified gases supply, or any combination thereof.

12. An apparatus as claimed in claim 1, wherein the sensors are disposed within a portion of the gases supply passage that is formed as an elbow with the sensors at or adjacent a bend of the elbow.

13. An apparatus as claimed in claim 1, wherein the sensors are located in a location where liquids may accumulate in the gases supply passage.

14. An apparatus as claimed in claim 1, wherein the second temperature sensor is spaced apart from the first sensor, one of the first temperature sensor and the second temperature sensor is located in a location where liquids may accumulate in the gases supply passage and the other being located in a location where liquids will not accumulate in the gases supply passage, the controller being adapted to calculate an estimate of relative humidity of gases flowing through the gases supply passage on a basis of the output from the first temperature sensor and the output from the second temperature sensor.

15. An apparatus as claimed in claim 1, wherein the first and second temperature sensors are located at a location along a gases supply conduit to a patient, adjacent the patient, adjacent the humidifier or intermediate along the gases supply passage.

16. An apparatus as claimed in claim 1, wherein the humidified gases supply includes a humidifier with a heater and a reservoir for containing a volume of water adjacent the heater.

17. An apparatus as claimed in claim 16, wherein the humidifier includes a heater plate and the reservoir comprises a removable container that contacts the heater plate in use.

18. An apparatus as claimed in claim 16, wherein the humidified gases supply includes a blower, an output of the blower being provided to an inlet of the humidifier.

19. An apparatus as claimed in claim 18, wherein the blower and the humidifier heater are arranged in a single housing.

20. An apparatus for the supply of humidified gases to a patient, the apparatus comprising:

a gases supply passageway defined by an inside surface of a passage wall and positioned upstream of a user interface, first and second temperature sensors embedded in or contacting an outside surface of the passage and does not extend through the inside surface of the wall of the gas supply passage wall of the passageway, a controller receiving outputs from the first and second temperature sensors and adapted to derive from the outputs of the first and second temperature sensors an estimation of humidity of gases flowing through the passageway or a control output for a humidified gases supply, wherein at least the inside surface of the passage wall separates the first and second temperature sensors from a flow of gases within the gases supply passageway such that the sensors sense temperature of the gases supply through at least the inside surface of the wall of the gases supply passage.

21. An apparatus as claimed in claim 1, wherein the temperature sensors are thermistors sensor is a thermistor.

22. An apparatus as claimed in claim 1, wherein the gases supply passage is a conduit.

23. An apparatus as claimed in claim 1, wherein the sensors are located in a location of the gases supply passage extending in a non-horizontal direction.

24. An apparatus as claimed in claim 1, wherein the sensors are located in a location of the gases supply passage extending in a substantially horizontal direction.

25. An apparatus as claimed in claim 12, wherein the elbow is located at a location adjacent to an exit port of the humidified gases supply.

26. An apparatus for the supply of humidified gases to a patient, the apparatus comprising:
  a humidified gases supply,
  a gases supply passage downstream of the humidified gases supply and upstream of the patient in use, the gases supply passage comprising a wall having an outside, and an inner surface
  first and second temperature sensors embedded in or located on the outside of the wall of the gases supply passage, and does not extend through the inner surface of the wall of the gas supply passage
  a controller receiving outputs from the first and second temperature sensors and adapted to derive from the outputs of the first and second temperature sensors an estimation of humidity of gases flowing through the gases supply passage and to provide a control output to the humidified gases supply according to the outputs of the first and second temperature sensors;
  wherein at least the inner surface of the wall of the gases supply passage separates the sensors from a flow of gases in the gases supply passage such that the sensors sense temperature of the gases supply through at least the inner surface of the wall of the gases supply passage, the sensors are disposed in a recess in an exterior surface of the wall of the gases supply passage, and the recess projects into a flow path of gases flowing through the gases supply passage to an extent not more than 30% of a diameter of the gases supply passage.

27. An apparatus as claimed in claim 26, wherein the diameter of the gases supply passage is between 10 mm and 30 mm.

28. An apparatus for the supply of humidified gases to a patient, the apparatus comprising:
  a humidified gases supply,
  a gases supply passage downstream of the humidified gases supply and upstream of the patient in use, the gases supply passage comprising a wall having an outside, and an inner surface
  first and second temperature sensors embedded in or located on the outside of the wall of the gases supply passage, and does not extend through the inner surface of the wall of the gas supply passage
  a controller receiving outputs from the first and second temperature sensors and adapted to derive from the outputs of the first and second temperature sensors an estimation of humidity of gases flowing through the gases supply passage and to provide a control output to the humidified gases supply according to the outputs of the first and second temperature sensors;
  wherein at least the inner surface of the wall of the gases supply passage separates the first and second temperature sensors from a flow of gases in the gases supply passage such that the sensors sense temperature of the gases supply through at least the inner surface of the wall of the gases supply passage, the first and second temperature sensors are disposed in a recess in an exterior surface of the wall of the gases supply passage, and a portion of the gases supply passage in an immediate vicinity of the sensors are formed from a material having a thermal conductivity at 25° C. less than 1 W/mK.

29. An apparatus as claimed in claim 28, wherein the portion of the wall of the gases supply passage in the immediate vicinity of the sensor is made from a plastic material.

30. An apparatus as claimed in claim 2, wherein the recess is accommodated within a general thickness of the wall of the passage.

31. An apparatus as claimed in claim 7, wherein the controller is adapted to compare the sensor outputs, or a derivative of the sensor outputs, and if different the controller indicates an error and/or operates in a safety mode.

32. An apparatus as claimed in claim 1, wherein the first and second sensors are located in a portion of the wall of the passage that is remote from the humidified gases supply, at a location along a gases supply conduit to a patient, adjacent the patient or intermediate along the passage.

33. An apparatus as claimed in claim 1, wherein the controller is adapted to compare the sensor outputs to each other, or a derivative of the sensor outputs, and if different the controller indicates an error and/or operates in a safety mode.

34. An apparatus as claimed in claim 1, wherein the first and second sensors sense temperature at an outlet of the humidifier.

* * * * *